United States Patent [19]

Jacob

[11] 4,061,589

[45] Dec. 6, 1977

[54] CORROSION INHIBITOR FOR COOLING WATER SYSTEMS

[75] Inventor: Jose T. Jacob, Waukegan, Ill.

[73] Assignee: Chemed Corporation, Cincinnati, Ohio

[21] Appl. No.: 759,361

[22] Filed: Jan. 17, 1977

[51] Int. Cl.$^2$ ............................................. C09K 3/00
[52] U.S. Cl. ........................... 252/389 A; 252/8.55 E; 21/2.5 A; 21/2.7 A
[58] Field of Search ................ 252/389 A, 8.55 E, 68, 252/147, 75; 21/2.5 A, 2.7 A

[56] References Cited

U.S. PATENT DOCUMENTS

| | | | |
|---|---|---|---|
| 3,803,047 | 4/1974 | Hwa | 252/389 A |
| 3,803,048 | 4/1974 | Hwa | 252/389 A |
| 3,859,396 | 1/1975 | Alink | 252/389 A |
| 3,935,125 | 1/1976 | Jacob | 252/8.55 E |
| 3,969,260 | 7/1976 | Clark | 252/389 A |
| 3,984,203 | 10/1976 | Alink | 21/2.7 A |

*Primary Examiner*—Leland A. Sebastian
*Assistant Examiner*—Josephine Lloyd
*Attorney, Agent, or Firm*—Charles L. Harness

[57] ABSTRACT

The invention disclosed relates to new improved corrosion inhibitors for cooling water systems, preparation thereof and use to inhibit metal corrosion in aqueous systems. The present corrosion inhibitors are 1,3,5-triazine-4,6-diketo 2-dithio ammonium phosphamate and 1,3,5-triazine 4,6-dithio 2-dithio ammonium phosphamate.

13 Claims, No Drawings

CORROSION INHIBITOR FOR COOLING WATER SYSTEMS

This invention relates to a new corrosion inhibitor, method for preparation thereof and use for preventing corrosion of metal surfaces in contact with aqueous systems.

Generally stated in the present corrosion inhibitor may be defined as 1,3,5-triazine 4, 6-diketo 2-dithio ammonium phosphamate and water-soluble metallic complexes thereof. This new corrosion inhibitor may be prepared by reacting a urea compound and phosphorous pentasulfide. The urea compound may be urea, substituted urea, or thiourea as desired.

In use, corrosion of metals may be prevented in contact with aqueous liquids by inclusion of the present corrosion inhibitor alone or in combination with zinc containing salts. Further, combinations of the present corrosion inhibitor and zinc with certain deposit-controlling agents prove to be highly effective in preventing corrosion while inhibiting sludge deposit in circulating water systems.

The method of this invention for preventing corrosion of metals in contact with an aqueous liquid comprises maintaining in the aqueous liquid from 1 to 10,000 ppm. of 1,3,5-triazine 4,6-diketo 2-dithio ammonium phosphamate, or of 1,3,5-triazine 4,6-dithio 2-dithio ammonium phosphamate, and preferably from 10 to 1,000 ppm thereof. It is recognized that the present corrosion inhibitor may be added to the aqueous liquid in various forms such as a metal complex, this substituted member or the like.

In addition to the present phosphamate corrosion inhibitor, additional materials may be effectively added. For example, corrosion inhibiting may be further improved by inclusion in the added ingredients of from about 1 to about 80 weight percent of an organophosphonic acid having one of the following formulae A, B or C:

Formula A
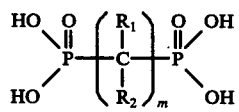

or

Formula B
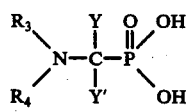

or

Formula C
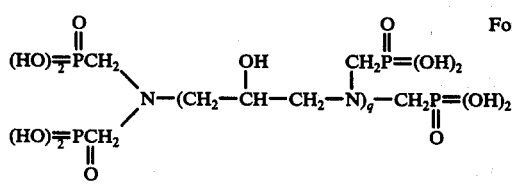

wherein $m$ is an integer from 1 to 10; $R_1$ is hydrogen, or an alkyl group having from 1 to 4 carbons; $R_2$ is hydroxyl, amino, hydrogen, or an alkyl group having from 1 to 4 carbons; $R_3$ is a member selected from the group consisting of hydrogen, hydroxyl, hydroxy alkyl groups containing from 1 to 4 carbon atoms, aliphatic groups containing from 1 to 30 carbon atoms, and

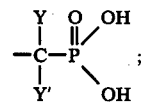

$R_4$ is a member selected from the group of hydrogen, aliphatic groups containing from 1 to 30 carbon atoms,

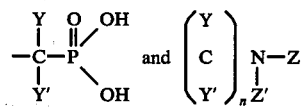

wherein $n$ is an integer from 1 to 30; Y and Y' are members selected from the group consisting of hydrogen and lower alkyl groups containing from 1 to 4 carbon atoms; Z is a member selected from the group consisting of hydrogen and

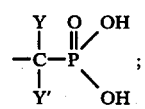

and Z' is a member selected from the group consisting of hydrogen,

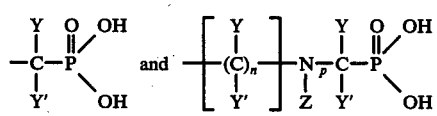

wherein $p$ is an integer from 1 to 30; with at least one of the groups represented by $R_3$ and $R_4$ containing at least one

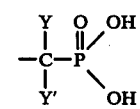

group; $q$ is an integer from 1 to 10 carbons, and the water-soluble salts and esters thereof; or mixtures thereof, and from 1 to 95 weight percent of a water-soluble zinc salt.

The present composition may include from about 1 to about 40 percent by weight of a water-soluble polymer such as polyacrylic acid, polymethacrylic acid, acrylic acid, methacrylic acid copolymers, hydrolyzed polyacrylamide, hydrolyzed polymethacrylamide, hydrolyzed acrylamide-methacrylamide copolymers, hydrolyzed polyacrylonitrile, hydrolyzed polymethacrylonitrile, hydrolyzed acrylonitrile-methacrylontrile copolymers, or mixtures of any two or more of the said polymers. Water-soluble salts of these polymers, or polymer mixtures may be used such as the respective alkali metal (e.g., sodium, potassium), and ammonium or amine salts.

The acrylic polymer builder component has a weight average molecular weight of from about 1,000 to about 15,000,000 and is preferably within the range of from 1,000 to 120,000. The preferred polymer is polyacrylic acid or sodium poly-metha acrylate having a weight average molecular weight within the range of 80,000 to 120,000. These polymers are commercially available, and methods for their preparation are well known in the art. The polyacrylate builder ingredient constitutes about 1 to about 40 percent by weight of the composition.

Alkali metal gluconate in amount of about 1 to about 20 percent by weight may be included in the present composition. The alkali metal gluconates include both the sodium and potassium salts thereof.

The composition of this invention may be prepared and stored or used as a dry powder or granular mixture, as tablets or like agglomerates, or in aqueous solutions containing up to 90 or 95 percent by weight, based on total solution weight, of water or water-cosolvent (e.g. alcohol) mixtures.

The compositions of this invention are useful for treating a variety of aqueous systems, that is, any aqueous system corrosive to metal surfaces in contact therewith. Suitable systems which can be treated according to this invention include water treatment systems, cooling towers, water circulating systems, and the like wherein fresh water, brines, sea water, sewage effluents, industrial waste waters, and the like are circulated in contact with metal surfaces. These compounds are useful in acid pickling baths, radiator coolers, hydraulic liquids, antifreezes, heat transfer mediums, and petroleum well treatments. The process of this invention is suitable for reducing the corrosion of iron, copper, aluminum, zinc and alloys containing these metals such as steel and other ferrous alloys, brass, and the like which are in contact with corrosive aqueous systems.

The compositions of this invention are non-toxic and prevent corrosion of metals in contact with aqueous liquids. These compositions can be substituted for chromate base corrosion inhibitors previously used where the toxicity of the chromate makes its use undesirable or where disposal of corrosion inhibiting solutions containing chromates raises serious water pollution problems requiring extensive pretreatment to remove the chromates prior to disposal of such solutions. The compositions of this invention in aqueous solutions prevent corrosion of metal parts such as heat exchangers, engine jackets, and pipes and particularly prevent metal loss, pitting, and tuberculation of iron base alloys, copper alloys, and aluminum alloys in contact with water.

All concentrations are given herein as weight percents unless otherwise specified.

Preferred organo-phosphonic acid compound for use in the composition of this invention is an alkylene diphosphonic acid having the foregoing Formula A, such as those disclosed in U.S. Pat. Nos. 3,214,454 and 3,297,578, the entire disclosures of which are incorporated herein by reference. Also suitable is an alkylene diphosphonic acid having the foregoing Formula B or Formula C such as those disclosed in U.S. Pat. No. 3,303,139, the entire disclosure of which is incorporated herein by reference. Suitable acids of this type include methylenediphosphonic acid; ethylidenediphosphonic acid; isopropylidenediphosphonic acid; 1-hydroxy, ethylenediphosphonic acid; hexamethylenediphosphonic acid; trimethylenediphosphonic acid; dicamethylenediphosphonic acid; 1-hydroxy, propylidenediphosphonic acid; 1,6-dihydroxy, 1,6-dimethyl, hexamethylenediphosphonic acid; 1,4-dihydroxy, 1,4-diethyl, tetramethylenediphosphonic acid; 1,3-dihydroxy, 1,3-dipropyl, trimethylenediphosphonic acid; 1,4-dibutyl, tetramethylenediphosphonic acid; dihydroxy, diethyl, ethylenediphosphonic acid; 4-hydroxy, 6-ethyl, hexamethylenediphosphonic acid; 1-hydroxy, butylidenediphosphonic acid; butylidenediphosphonic acid; 1-aminoethane-1,1-diphosphonic acid; 1-aminopropane-1,1-diphosphonic acid; 1-aminobenzyl-1,1-diphosphonic acid; 1,6-diaminohexane-1,1,6,6-tetraphosphonic acid; 1-aminoethane 1,1-diphosphonic acid monoethyl ester, and 1-amino - 2 -phenylethane -1,1-diphosphonic acid. The water-soluble salts of these acids such as the alkali metal, alkaline earth metal, zinc, cobalt, chromium, lead, tin, nickel, ammonium, or amine and lower alkanol amine salts can be used. Also, esters of these acids with an aliphatic alcohol having from 1 to 4 carbons, or mixtures of the above acids, salts or esters can be used. Use of mixtures of any of the general types of organo-phosphonic acid compounds described above is also contemplated. A number of these compounds can be described as methanol phosphonic acid derivatives having the following Formula D:

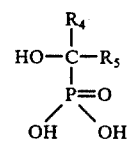

Formula D where $R_4$ is independently selected from the group consisting of an alkyl group up to four carbon atoms and phosphonate groups, and $R_5$ is selected from the group consisting of alkyl groups having up to 4 carbon atoms, when $R_4$ is a phosphonate group and

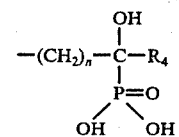

where $n$ is 0 to 6, when $R_4$ is an alkyl group; and water-soluble salts thereof.

Specific methanol phosphonic acid compounds thus disclosed include, for example, 1-hydroxy, ethylidene diphosphonic acid (i.e., ethanol, or methyl methanol, 1,1-diphosphonic acid);1-hydroxy, propylidene diphosphonic acid (i.e., ethyl methanol diphosphonic acid); 1,6-dihydroxy 1,6-dimethyl, hexamethylene diphosphonic acid (i.e., tetramethylene bis(methyl methanol phosphonic acid) and its sodium salt; 1,4-dihydroxy-1,4-diethyl, tetramethylene diphosphonic acid (i.e., dimethylene bis (ethylmethanol phosphonic acid)); 1,3-dihydroxy-1,3-dipropyl trimethylene disphosphonic acid (i.e., methylene bis (propylmethanol phosphonic acid)) and its sodium salt; dihydroxy, diethyl, ethylene diphosphonic acid (i.e., bis(ethylmethanol phosphonic acid) and its sodium salt; and 1-hydroxy butylidene diphosphonic acid (i.e., propyl methanol diphosphonic acid).

The present compositions may also contain from about 1 to 10 percent by weight of a water-soluble zinc salt.

The zinc salts which can be employed in the composition of this invention include any water-soluble zinc salt such as zinc sulfate, zinc chloride, zinc nitrate, alkali metal-zinc phosphate glasses, crystalline alkali metal-zinc poly-phosphates, and the like.

This invention is further illustrated by the following specific but non-limiting examples.

EXAMPLE 1

Preparation of 1,3,5-triazine-4, 6-diketo 2-dithio ammonium phosphamate was effected by heating at 100° C. equal molar portions of urea and phosphorus pentasulfide. The reaction proceeded by the following equation:

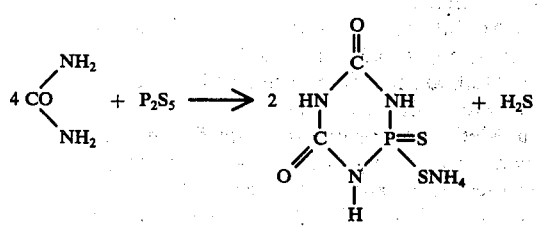

The product was then extracted with cold water. Colorless crystalls were isolated. The compound decomposed above 260°C. The infra-red spectrum postulates a tentative ring structure as suggested by Hemmelmayr Monatsh. 26, 772 (1905).

EXAMPLE 2

In the following tests, the water used had the following composition:

TABLE I

| Components | Value |
|---|---|
| Ca | 110 ppm |
| Mg | 51 ppm |
| HCO$_3$ | 185 ppm |
| CO$_3$ | None |
| OH | None |
| Cl | 492 |
| SO$_4$ | 630 |
| Total dissolved solids | 2006 ppm |
| pH | 6.6 |
| Langelier Index | 0.6 |

The tests used for this evaluation are described by H. Kerst in *Materials Protection and Performance*, Vol. 12, No. 8, p. 35, August 1973. The tests were run at a pH of 6.5 – 7.0, at a temperature of 100° F.

A comparison of the corrosion rates of the individual ingredients of the composition of this invention with combination of these ingredients according to this invention were found to be as shown in Table II and Table III.

TABLE II

Galvanic Measurements of Corrosion Current
Using a 1010 Steel Anode and Platinum Cathode

| Test No. | Additive | 24 Hour Corrosion Rate (MPY) |
|---|---|---|
| 1 | None | 70 |
| 2 | 5 ppm ZnSO$_4$ | 5 |
| 3 | 10 ppm TKTP | 6 |
| 4 | 10 ppm TKTP + 5 ppm ZnSO$_4$ | 1.5 |
| 5 | 20 ppm TKTP + 8 ppm Sodium Gluconate | 1.25 |
| 6 | 5 ppm ZnSO$_4$ + 8 ppm Sodium Gluconate | 6.5 |
| 7 | ZnSO$_4$ + 8 ppm Sodium Gluconate | 0.75 |

TABLE III

Using Model 1180 Corrater (Magna Corporation)

| Test No. | Additive | 24 Hour Corrosion Rate (MPY) |
|---|---|---|
| 1 | 20 ppm TKTP + 15 ppm ZnSO$_4$ + 16 ppm Sodium Gluconate | 1.2 |
| 2 | 20 ppm TKTP + 15 ppm ZnSO$_4$ + 16 ppm Sodium Gluconate + 10 ppm Dequest | 0.8 |
| 3 | 20 ppm TKTP + 15 ppm ZnSO$_4$ + 28 ppm Dequest | 0.45 |

*Dequest represents 60% Ethane - 1 hydroxy -1, 2-diphosphonic acid, a product of Monsanta Chemical Co.

EXAMPLE 3

The procedure of Example 1 was repeated except using thiourea in place of urea. The product made was considered to be the dithio analog of TKTP, viz. 1,3,5-triazine -4,6 -dithio-2 dithioammonium phosphamate ("thio-TKTP"), of the formula

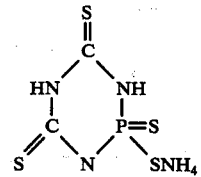

When tested using the procedure of Example 3, the recovered product was found to have at least corresponding results and in some cases, the results for corrosion inhibition exceeded those of Example 2.

EXAMPLE 4

In order to evaluate addition of thio-TKTP, i.e., the product of Example 3, against standard corrosion inhibitive formulas for cooling water, a simulated cooling tower test unit was used.

The test used for this evaluation is that described by Hwa, C. M. "New Inhibitor Developed for Open Recirculating Cooling Water Systems", Materials Protection and Performance, volume 9, no. 7, pages 29–31 (1970) July. The tests were run at a pH of 8-8.5 at a temperature of 130° F. with a flow rate of 1.5 ft. per second past the specimens. In one group of tests, the treatment which was used was 100 ppm of a formula containing Dequest 2010, sodium heptagluconate, sodium metasilicate, sodium benzoate, a lignin derivative, mercaptobenzothiazole and benzotriazole. These tests were run for 10 days, starting out with a 5 x pretreatment of the formula. The average corrosion rate found on three steel coupons at the end of the 10 day test was 12.2 MPY. A similar test was run using the same formula but adding 10 ppm of thio-TKTP or 10 ppm TKTP of Example 3. The average corrosion rate shown by two steel coupons at the end of 10 days was 5.2 MPY.

A similar pair of tests were run using 100 ppm of a similar formula containing sodium benzoate, benzotriazole, sodium silicate, Dequest 2010, mercaptobenzothiazole, sodium glucoheptanate, a lignin derivative, and polyethylene glycol 400 monoleate. The average corrosion rate shown by three steel specimens at the end of 10 days was 16.3 MPY. In a test, to which was added 10 ppm of thio TKTP or 10 ppm TKTP of Example 3, the average corrosion rate shown by two steel specimens at the end of 10 days was 2.7 MPY.

From the above it will be noted that thio TKTP and TKTP, while having corrosion inhibitive properties of their own, show their greatest utility in combinations with other materials.

Concentrations recommended are:

|  | Broad range, ppm. | Preferred range, ppm. |
|---|---|---|
| TKTP or thio-TKTP Phosphonate, or ester or salt | 1 – 10,000 | 10 – 1,000 |
| thereof | 0 – 6,000 | 6 – 600 |
| Water-soluble zinc salt | 0 – 5,000 | 5 – 500 |
| Water-soluble polymer | 0 – 2,500 | 2 – 250 |
| Alkali-metal gluconate | 0 – 3,000 | 3 – 300 |

It is understood that the foregoing detailed description is given merely by way of illustration and that many variations may be made therein without departing from the spirit of this invention.

Some preferred embodiments of the composition to be added to water include the following.

A. The composition consists essentially of a member selected from the group consisting of 1,3,5-triazine 4,6-diketo-2-dithio ammonium phosphamate and 1,3,5-triazine 4,6-dithio-2-dithio ammonium phosphamate and 5 to 50 parts of a water-soluble zinc salt per part of said triazine group member.

B. The composition of (A) may contain additionally an alkali metal gluconate in a weight ratio of 0.3 to 30 parts to 1 part of the triazine group member.

C. The composition of (A) may contain additionally a member selected from the group consisting of phosphonates and their esters and salts in a weight ratio of 0.6 to 60 parts to 1 part of the triazine group member.

D. The composition of (B) may contain additionally a water soluble polymer in a weight ratio of 0.2 to 25 parts to 1 part of the triazine group member.

What is claimed is:

1. The method of inhibiting metal corrosion in aqueous systems that comprises adding to the aqueous liquid an effective amount, 1 –10,000 ppm. of a member selected from the group consisting of 1,3,5-triazine-4,6-diketo-2-dithio ammonium phosphamate and 1,3,5-triazine-4-6-dithio-2-dithio ammonium phosphamate.

2. Method according to claim 1 in which the group member is 1,3,5- triazine-4,6diketo-2-dithio ammonium phosphamate.

3. Method according to claim 1 in which the group member is 1,3,5-triazine-4,6-dithio-2-dithio ammonium phosphamate.

4. Method according to claim 1 which 10–1,000 ppm of the group member is added.

5. Method according to claim 1 in which 5 to 500 ppm of a water-soluble zinc salt is also added.

6. Method according to claim 5 in which a member selected from the group consisting of phosphonic acids and their esters and salts is also added.

7. Method according to claim 1 in which 3 to 300 ppm, of an alkali metal gluconate is also added.

8. Method according to claim 1 in which 6 to 600 ppm of a member selected from the group consisting of phosphonic acids and their esters and salts is also added.

9. Method according to claim 5 in which about 10 to 1000 ppm of 1,35-triazine-4,6-diketo-2-dithio ammonium phosphamate, 5 to 500 ppm zinc sulfate, and about 6 to 600 ppm sodium gluconate are added.

10. Corrosion-inhibiting composition consisting essentially of a member selected from the group consisting of 1,3,5-triazine 4,6-diketo-2-dithio ammonium phosphamate and 1,3,5-triazine-4,6-dithio-2-dithio ammonium phosphamate and 5 to 50 parts of a water-soluble zinc salt to one part of said group member.

11. Composition according to claim 10 containing additionally an alkali metal gluconate in a weight ratio of 0.3 to 30 parts to 1 part of the triazine group member.

12. Composition according to claim 10 containing additionally a water soluble polymer in a weight ratio of phosphonates and their esters and salts in a weight ratio of 0.6 to 60 parts to 1 part of the triazine group member.

13. Composition according to claim 11 containing additionally an alkali metal gluconate in a weight ratio of 0.2 to 25 parts to 1 part of the triazine group member.

* * * * *